(12) United States Patent
Mikubo et al.

(10) Patent No.: US 6,238,086 B1
(45) Date of Patent: May 29, 2001

(54) METHOD OF CALCULATING THERMAL RESISTANCE IN SEMICONDUCTOR PACKAGE ACCOMMODATING SEMICONDUCTOR CHIP WITHIN A CASE WHICH CAN BE APPLIED TO CALCULATION FOR SEMICONDUCTOR PACKAGE WITH RADIATION FINS

(75) Inventors: Kazuyuki Mikubo; Sakae Kitajo, both of Tokyo (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 09/239,835

(22) Filed: Jan. 29, 1999

(30) Foreign Application Priority Data

Feb. 2, 1998 (JP) .................................. 10-021063

(51) Int. Cl.$^7$ ........................... G01N 25/18; G01N 25/20
(52) U.S. Cl. ........................ 374/43; 702/132; 702/136; 374/44
(58) Field of Search ............................. 374/43, 44, 141; 702/130, 136, 132, 133, 134, 135, FOR 142; 703/2, 3, 5, 6, 7, 12

(56) References Cited

U.S. PATENT DOCUMENTS

| | | | |
|---|---|---|---|
| 4,713,612 | * 12/1987 | Takamine | 374/44 |
| 5,051,865 | * 9/1991 | Kato | 361/718 |
| 5,581,489 | * 12/1996 | Groothuis et al. | 703/2 |
| 5,604,687 | * 2/1997 | Hwang et al. | 702/136 |

FOREIGN PATENT DOCUMENTS

| | | |
|---|---|---|
| 64-13445 | 1/1989 | (JP) . |
| 5-151324 | 6/1993 | (JP) . |

OTHER PUBLICATIONS

Weed, K.; Kirkpatrick, A., "Thermal evaluation of /spl Theta//sub JA/ for varying board conductivity," Proc. 46th Electronic Components and Technology Conference, 1996, pp. 792–797.*

Edwards, D., et al., "Thermal enhancement of IC packages," Proc. SEMI–THERM X., 1994, pp. 33–43.*

Sullhan, R., et al., "Thermal modeling and analysis of pin grid arrays and multichip modules," Proc. SEMI–THERM VII., 1991, pp. 110–116.*

Electronic Mounting Technology; Basic Platform, vol. 6; Design/Reliability Evaluation Technology (corp.) Industrial Survey Association; Feb. 1, 1995; in particular, PP. 217–220 and 198–202, (Partial Translation).

Yang, et. al., "Validation Study of Compact Thermal Resistance Models of IC Packages", IEEE 1996 Electronic Components and Technology Conference, pp 165–171.

* cited by examiner

Primary Examiner—Diego Gutierrez
Assistant Examiner—Stanley J. Pruchnic, Jr.
(74) Attorney, Agent, or Firm—McGinn & Gibb, PLLC

(57) ABSTRACT

The thermal resistance of an entire semiconductor package with a semiconductor chip and radiation fins is calculated based on thermal resistance of resin between the semiconductor chip and case, thermal resistance of the radiation fins, and thermal resistance of three heat radiation paths in the semiconductor package. One of said three heat radiation paths is passing through the bottom surface of the case. The other of said three radiation paths is passing through the leadframe. The other of three radiation paths is passing through sides of the case other than the leadframe.

17 Claims, 6 Drawing Sheets

FIG. 7
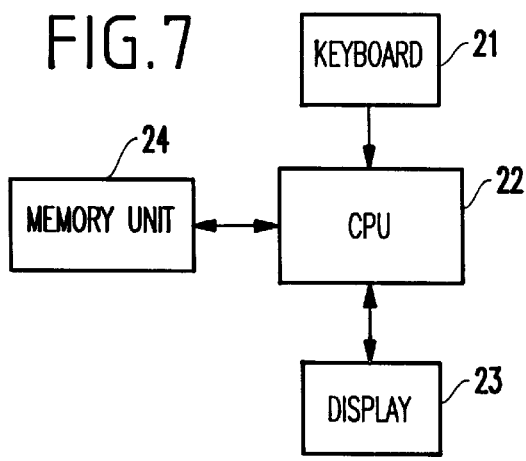
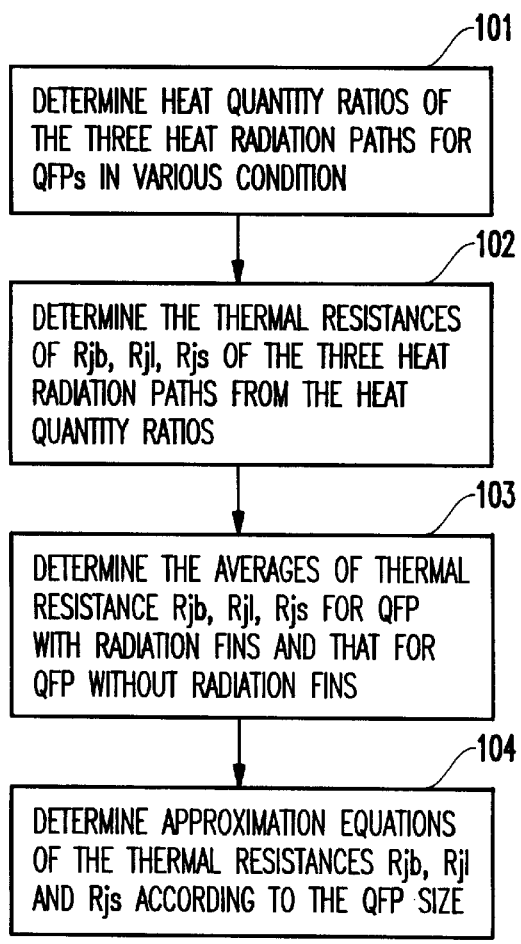
FIG. 8

METHOD OF CALCULATING THERMAL RESISTANCE IN SEMICONDUCTOR PACKAGE ACCOMMODATING SEMICONDUCTOR CHIP WITHIN A CASE WHICH CAN BE APPLIED TO CALCULATION FOR SEMICONDUCTOR PACKAGE WITH RADIATION FINS

BACKGROUND OF THE INVENTION

1. Field of the Invention

The present invention relates to a thermal resistance calculation method and device for calculating the thermal resistance of a semiconductor package in which a semiconductor chip is incorporated within a case.

2. Description of the Related Art

Among the problems such as failures in operation that typically occur in electronic components, problems originating from heat generally occur due to increase in localized temperatures in electronic components. With the increasing density of electronic components that has accompanied the decreasing size of electronic equipment in recent years, temperature can increase significantly within a short range. In other words, these problems are caused by increase in calorific density. Conventionally, rough estimates of temperature are made for each electrical component in the design stage and components are then fabricated with due consideration given to temperature variation. With the increase in heat density, however, the actual heat conditions may exceed the temperatures estimated in the design stage, and problems including malfunctioning and failure may therefore occur.

For electrical parts mounted in electrical equipment, therefore, temperature estimates must be made stringently for each individual electrical component, and the design of cooling devices (including the choice and placement of heat radiation fins, fans, etc.) must be based on these temperature estimates. Thermal resistance must be accurately determined to predict temperatures in semiconductor packages, which are electrical parts that generate heat. One method of the prior art for precisely determining thermal resistance in a semiconductor package is disclosed in "Validation Study of Compact Thermal Resistance Models of IC Packages" by Zemo Yang and Young Kwon in IEEE 1996 Electronic Components and Technology Conference, pages 165–171. According to this method, the surface temperatures of parts, substrates, and heat radiation equipment are first found by using a thermocouple, the junction temperature of a semiconductor package is estimated by using the voltage drop across the base and emitter of a transistor, and these temperatures are inserted in the various compact thermal resistance models shown in FIGS. 1A–1C. The thermal resistance of a semiconductor package itself has conventionally been found by methods using such compact thermal resistance models, and the thermal resistance thus determined are reflected in the design of cooling equipment.

Since heat generation in electrical components such as semiconductor packages causes problems in electronic components as described in the foregoing description, radiation fins are often mounted on the surface of case of semiconductor package to release the heat of the semiconductor package. However, radiation fins are not included in the above-described compact thermal resistance models shown in FIGS. 1A–1C. In other words, the thermal resistance of a semiconductor package with radiation fins mounted cannot be determined by the prior-art method of finding thermal resistance by using these compact thermal resistance models. The prior art includes cases in which the thermal resistance of a semiconductor package without radiation fins and the thermal resistance of radiation fins were each found separately, but thermal resistance in a case in which the two are unified has not been considered, and a calculation method has not been established. Mounting radiation fins on the case should change the thermal resistance of the path passing through the surface of case on which radiation fins are mounted, but this altered thermal resistance has not been found in the prior art. Although cooling devices may be designed based on the thermal resistance of a semiconductor package unit lacking radiation fins and the thermal resistance of the radiation fins unit, such an approach may not realize the optimum design.

In the above-described method of the prior art, moreover, the thermal resistance of a semiconductor package is found based on the measurements of various temperatures for one type of semiconductor package, and a change in any one of the factors that influence thermal resistance, such as the size of the semiconductor package, the size of the semiconductor chip, and the resin material that fills the inside of the semiconductor package, necessitates the repetition of the measurement of temperatures and associated calculations. The measurement results and calculation results for the thermal resistance computation relating to one type of semiconductor package therefore cannot be applied to another type of semiconductor package. Each and every measurement and calculation of the temperatures of the various points of the semiconductor package must be carried out whenever calculating for electronic components that are not exactly the same. The preparatory work necessary for designing electronic equipment is therefore extremely complicated, and this complexity both increases manufacturing costs and lengthens the time necessary to design and manufacture electronic equipment. The problem therefore exists that conventional methods cannot keep pace with the short life cycles of the recent products.

Although not described in detail, there is a method of finding the thermal resistance of a semiconductor package by a three-dimension heat-fluid simulation in which a three-dimensional problem of heat and fluid is solved by making use of a difference method or finite-element method based on the laws of conservation of mass (continuity equation), conservation of momentum (Navier-Stokes equation), and conservation of energy (conservation of energy equation). This method can be applied to determination the thermal resistance of a semiconductor package with radiation fins. In this method, however, as with the above-described prior art, the three-dimensional heat-fluid simulation must be repeated from the beginning if there is any change in any one of the factors that affect thermal resistance, such as the size of the semiconductor package or semiconductor chip or the material of the resin. If absolutely identical semiconductor packages are not used, therefore, the design of each electronic component necessitates extremely laborious procedures such as measurements of temperatures and calculations, meaning that a great deal of time is required for the design and manufacture of electronic component, and the resulting products are not sufficiently adaptable for the ever-shortening life cycle of product. In particular, methods in which such a three-dimensional heat-fluid simulation is carried out require special expertise in order to apply a difference method or finite-element method to partition meshes or set boundary conditions. These methods are therefore not easily used by anyone lacking expert knowledge, and in addition, are difficult because each and every electronic component must be individually designed.

SUMMARY OF THE INVENTION

It is an object of the present invention to provide a thermal resistance calculation method that would allow even a person lacking specialized knowledge to quickly and easily calculate the thermal resistance of a semiconductor package on which radiation fins are mounted, regardless of changes in such conditions as the shape of the semiconductor package.

According to the present invention, the thermal resistance of a semiconductor package on which radiation fins are mounted can be quickly and easily found because thermal resistance of a semiconductor package in which a semiconductor chip is accommodated inside a case is found based on the following thermal resistance. One of them is the thermal resistance of the path of heat radiation through the bottom surface of the case, another of them is the thermal resistance of the path of heat radiation through a leadframe, another of them is the thermal resistance of the path of heat radiation through sides of the case other than the leadframe, another of them is the thermal resistance between the semiconductor chip and case surface, and another of them is the thermal resistance of the radiation fins.

The thermal resistance calculating device of this invention includes an input means, a processing means, and a display means; and the processing means is for finding the thermal resistance of a semiconductor package on which radiation fins are mounted based on the above-described calculation method. To find this thermal resistance by the processing means, at least the size of the semiconductor package, the size of the semiconductor chip, and thermal resistance of the radiation fins are inputted from the input means. The display means displays thermal resistance of the semiconductor package found by the processing means. This thermal resistance calculation method displays the thermal resistance of a semiconductor package under a number of conditions when these conditions are input and therefore enables the prediction of the thermal resistance of a product that has not actually been fabricated, thus enabling optimization of the product design.

The above and other objects, features, and advantages of the present invention will become apparent from the following description with references to the accompanying drawings which illustrate examples of the present invention.

BRIEF DESCRIPTION OF THE DRAWINGS

FIG. 7 is a block diagram showing the thermal resistance calculating device of the present invention;

FIG. 8 is a flow chart showing the preparatory steps of the thermal resistance calculating device of the present invention;

DETAILED DESCRIPTION OF THE PREFERRED EMBODIMENTS

Explanation is first presented regarding the various types of typical semiconductor packages.

Figure 2:
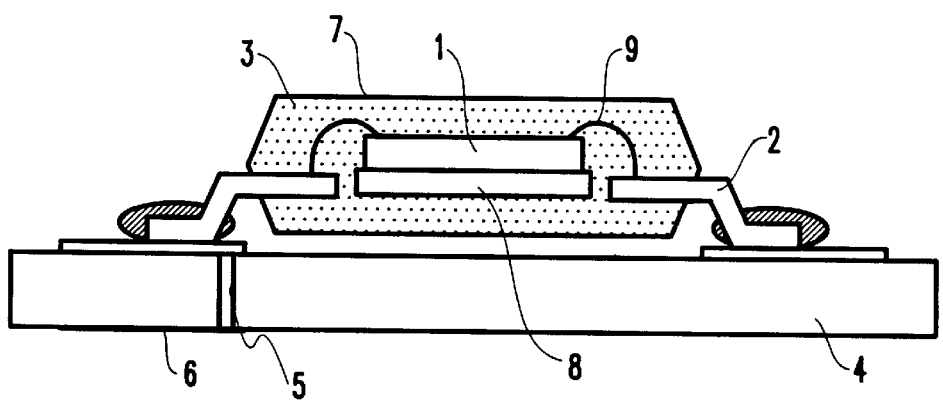
FIG. 2 is a sectional view showing the basic structure of a Quad Flat Package (QFP)

Referring to FIG. 2, the basic structure of such a semiconductor package is a structure wherein semiconductor chip 1 mounted on island 8 is molded in resin 3 inside case 7. Leadframe 2, which extends in four directions from the inside of case 7, is connected to semiconductor chip 1 by means of bonding wires 9. This type of semiconductor package is generally referred to as a quad flat package (hereinbelow abbreviated QFP). This QFP is mounted on wired substrate 4, and leadframe 2 is soldered and affixed to copper foil 6 forming a conductive pattern. Copper foil 6 is conductive with a pattern on the bottom surface of wiring substrate 4 by way of through-holes 5, and a double-sided substrate is thus formed.

Figure 3A:
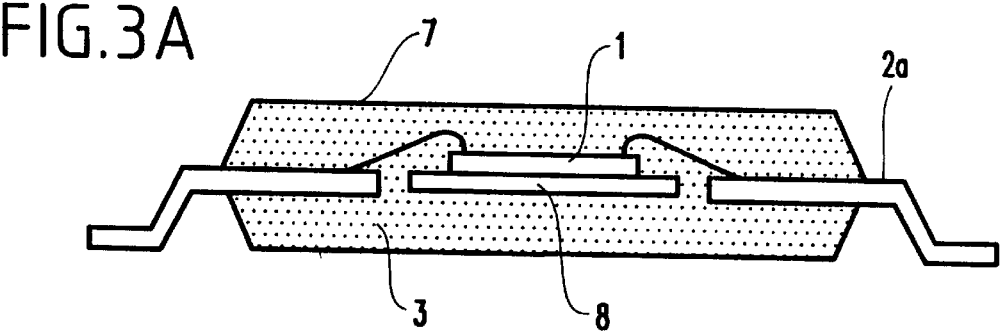
FIGS. 3A–3D are sectional views illustrating types of QFP.
Figure 3B:
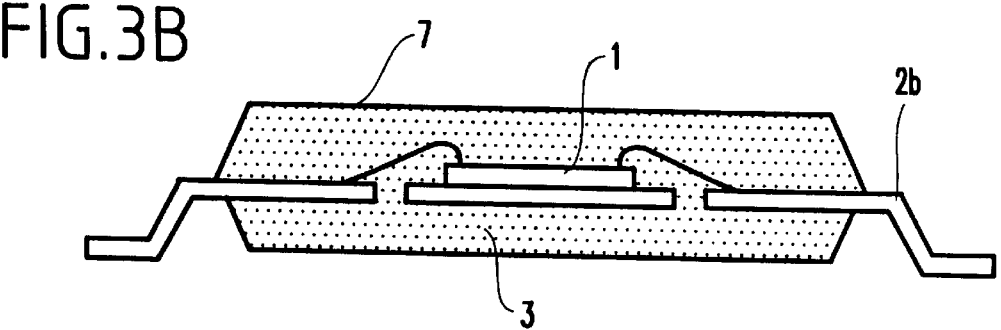

The internal structure of this type of QFP can be broadly divided between two types. Referring to FIGS. 3A and 3B, one type of QFP internal structure is the standard type in which only semiconductor chip 1 on island 8 and leadframe 2 are molded in resin 3 inside case 7. Categorizing this type in more detail, there is a type shown in FIG. 3A that is suited to be driven in low power consumption and having leadframe 2a made of 42-alloy (iron-nickel alloy), and a type shown in FIG. 3B that is suited to be driven in medium-scale power consumption and having leadframe 2b made of a copper alloy.

Figure 3C:
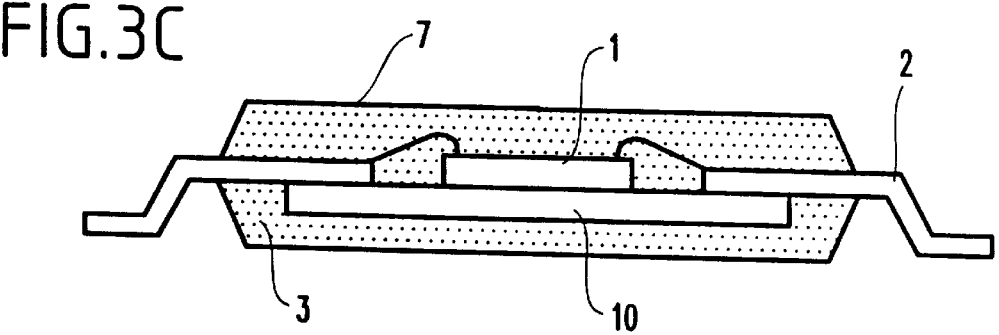
Figure 3D:
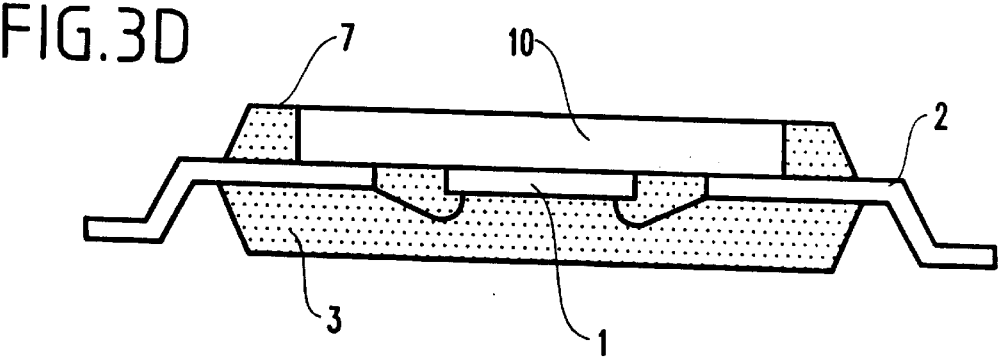

Referring to FIGS. 3C and 3D, another type of QFP is a heat-spreader type directed to high power consumption in which heat spreader 10 made of a metal plate is interposed between semiconductor chip 1 and leadframe 2 to efficiently radiate the heat of these components, these components all being molded by resin 3 inside case 7. This heat-spreader type can be further divided between a type in which heat spreader 10 is wholly enclosed within case 7 as shown in FIG. 3C, and a type in which heat spreader 10 is exposed to the outside as shown in FIG. 3D.

Figure 4:
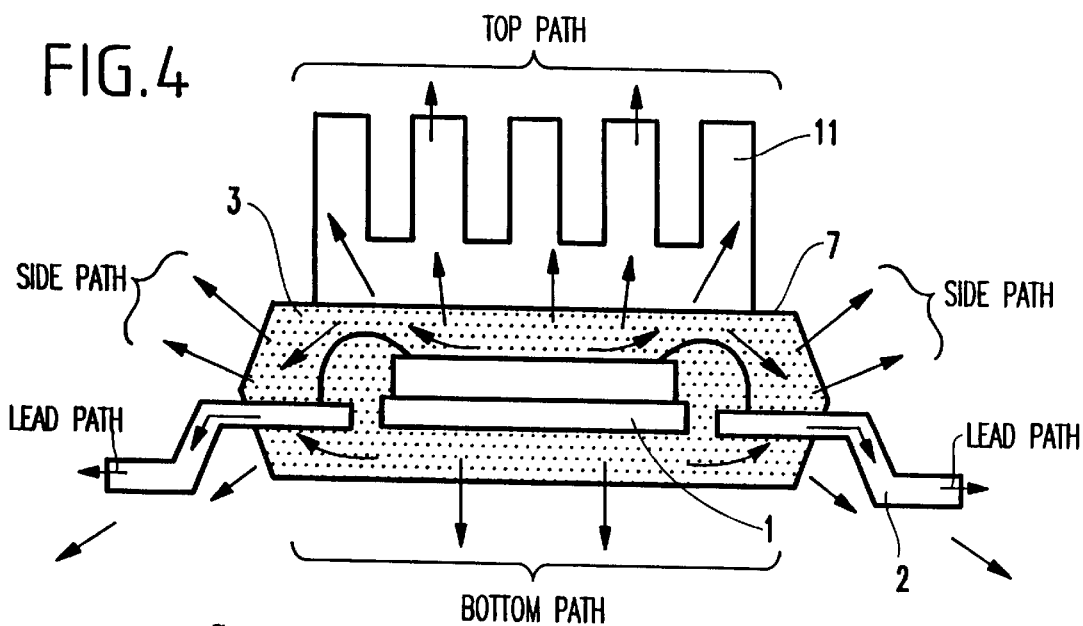
FIG. 4 is a sectional view showing heat radiation in a QFP on which radiation fins are mounted.

QFPs frequently include radiation fins 11 that are mounted on the surface of case 7 to release heat from semiconductor chip in order to avoid affecting other components outside, as shown in FIG. 4. A method is considered for calculating the thermal resistance of a QFP that includes radiation fins 11. Referring to FIG. 4, the heat generated by semiconductor chip 1 of a QFP is transmitted in various directions, making up a complex radiation pattern. These paths of heat radiation are considered by dividing them between a number of regions. Essentially, the paths by which heat generated from semiconductor chip 1 is finally transmitted into the air can be divided between four heat radiation paths: a path toward the top surface of the QFP (TOP path), a path toward the bottom surface (BOTTOM path), a path through the leadframe (LEAD path), and a path toward the sides of the case except the leadframe (SIDE path). The TOP path of these can be regard as to be joined path of a path from the heat-radiating portion of semiconductor chip 1 (although not clearly shown in FIG. 4, the heat-radiating portion of semiconductor chip 1 is referred to hereinbelow as the IC junction) to the surface of case 7, and a path by which heat passes to the air through the inside of radiation fins 11 on case 7.

Figure 1A:
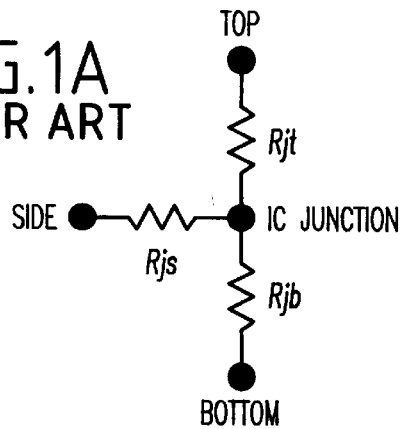
FIGS. 1A–1C show compact models of thermal resistance for finding the temperatures in a semiconductor package according to the prior art.
Figure 1B:
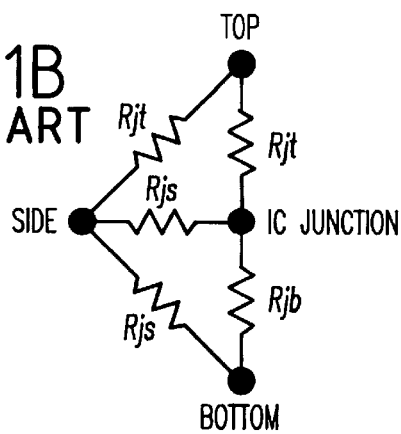
Figure 1C:
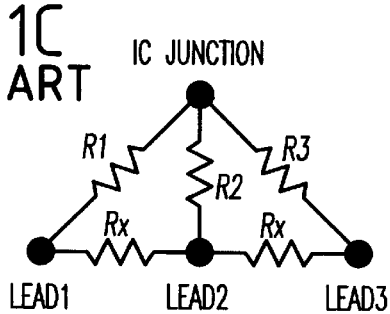
Figure 5:
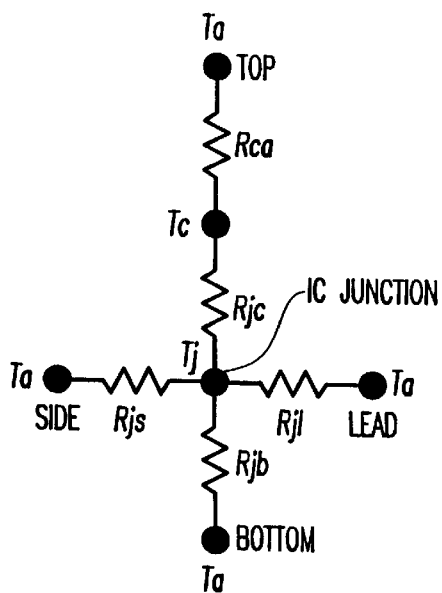
FIG. 5 shows a compact thermal resistance model illustrating the thermal resistance calculating method of the present invention.

Referring to FIG. 5, the heat radiation paths that are established in this invention are modeled in comparison with the example of the prior art shown in FIG. 1. The temperature of each portion is indicated as T, the thermal resistance of each interval is indicated as R, and affixes are added to indicate each portion. Namely, Tj is the IC junction temperature, Tc is the case surface temperature, and Ta is the ambient air temperature. The thermal resistance of the BOTTOM path from the IC junction to the bottom is Rjb, the thermal resistance of the LEAD path from the IC junction to the leadframe is Rjl, the thermal resistance of the SIDE path from the IC junction to the sides is Rjs, and, as for the TOP path, the thermal resistance from the IC junction to the case surface is Rjc, and the thermal resistance from the surface of case 7 to the ambient air is Rca. Thermal resistance Rca is the thermal resistance of the radiation fins 11 unit itself.

Conventionally, a QFP not having radiation fins attached has been considered as one independent component, and thermal resistance Rja of the QFP was found by taking thermal resistance Rjc from the IC junction to the surface of case 7 as thermal resistance Rjt of the TOP path. Radiation fins 11 were considered as a part separate from the QFP, and even if the thermal resistance of the fins alone was found, the relation between the thermal resistance of a QFP without radiation fins and the thermal resistance of the radiation fin unit was not considered. However, attaching radiation fins has an effect on the thermal resistance of the QFP, therefore the heat properties of such an electrical component having radiation fins cannot be accurately known even if the thermal resistance of each are separately determined. In response to this situation, in the present invention, a QFP is considered to be complete only after attachment of radiation fins 11 as for thermal resistance. In other words, in the present invention, a component with case 7 containing semiconductor chip 1 and leadframe 2 unified with radiation fins 11 is considered as a single electrical component (semiconductor package), and then calculations regarding thermal resistance is carried out.

Based on the above-described basic concept of the present invention, the total thermal resistance Rja of all heat radiation paths from the IC junction of a QFP to the ambient air can be found as follows:

$$1/Rja = [1/(Rjc+Rca)] + 1/Rjb + 1/Rjl + 1/Rjs \quad (1)$$

This equation (1) is found by trial and error. As for a number of QFPs of differing package types or characteristics, when the result of finding thermal resistance Rjc by means of equation (1) is compared with the result of finding thermal resistance Rjc by making use of specialized knowledge and carrying out three-dimensional heat-fluid simulation that solves three-dimensional problems of heat and fluids, the error of both results is small enough to be ignored for all tested QFPs, and this equation (1) is therefore considered to be widely applicable to various QFPs. Explanation is next presented regarding one concrete example of calculating thermal resistance of a QFP based on equation (1).

In this example, thermal resistance Rja was calculated for a standard type QFP having leadframe 2b made of a copper alloy both without fins, as in FIG. 3B, and with radiation fins 11 mounted such as shown in FIG. 4. The thermal resistances Rjb, Rjl, and Rjs of each of the heat radiation paths other than the TOP path were first investigated based on actually measured temperatures. The results are as follows.

|  | Rjb | Rjl | Rjs |
|---|---|---|---|
| QFP with Radiation fins | 62 | 1685 | 225 |
| QFP without radiation fins | 57 | 735 | 210 |

The absolute thermal resistance of the three heat radiation paths (BOTTOM, LEAD, and SIDE paths) shows little change regardless of whether radiation fins 11 were present or not present. The determination of thermal resistance Rja of the entire QFP therefore permits a calculation using the thermal resistance of the three paths in a state in which radiation fins are present, a calculation using thermal resistance of the three paths in a state in which radiation fins are not present, or even a calculation using the average values of thermal resistances in a state with radiation fins and a state without them. In this case, taking substantially averaged values of a state in which radiation fins are present and a state in which radiation fins are not present:

$Rjb = 60 (° C./W)$ $Rjl = 1210 (° C./W)$ $Rjs = 218 (° C./W)$

Thermal resistance Rjc is next found for this QFP. Generally, thermal resistance R between two opposing surfaces within a solid matter is found as follows:

$$R = L/(\lambda \cdot A) \quad (2)$$

$\lambda$ is the thermal conductivity of the material interposed between the two surfaces, L is the distance between the two surfaces, and A is the area of the surfaces.

As for the QFP used here, distance L=0.000945 (m), thermal conductivity $\lambda$=0.6 (W/mk) (the thermal conductivity of plastic), and area A=$(0.0136)^2$ ($m^2$), based on the length 13.6 mm of one side of the semiconductor chip. When these data are used in equation (2), Rjc is 8.52 (° C./W). Thermal resistance Rca of the radiation fin unit is 13.7 (° C./W).

The thermal resistance Rja of the QFP with radiation fins can be calculated by inserting into equation (1) each of thermal resistances Rjc, Rca, Rjb, Rjl, and Rjs of each portion found as described above, Namely Rja is 14.9 (° C./W).

On the other hand, while the process is not described in detail, the value for thermal resistance Rja found by three-dimensional heat-fluid simulation for this QFP was 14.7° C./W. The error for thermal resistance Rja found by equation (1) of this invention is therefore about only 1.3%, from which it can be seen that sufficient accuracy was obtained.

Figure 6A:
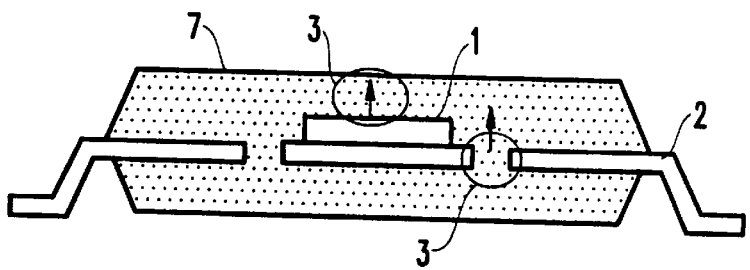
FIGS. 6A–6B are sectional views showing the heat radiation in a heat spreader-type QFP.
Figure 6B:
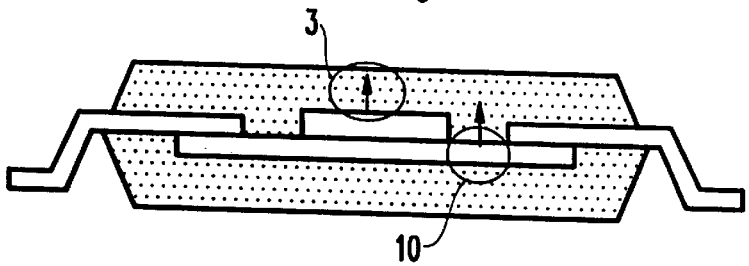

However, thermal resistance Rjc from the IC junction to the surface of case 7 of a heat-spreader type QFP cannot be found simply using equation (2). Namely, if heat spreader 10 made of a copper plate of high thermal conductivity is thermally coupled between semiconductor chip 1 and leadframe 2, heat is diffused throughout the entire QFP and the thermal resistance decreases. Referring to FIG. 6B, heat radiation by way of copper (heat spreader 10) between semiconductor chip 1 and leadframe 2 cannot be ignored in the heat-spreader type, so thermal resistance Rjc cannot be found by a simple process by using equation (2).

However, thermal resistance Rjc can be found by the following equation (3), which enables the determination of thermal resistance Rjc from semiconductor chip 1 to the surface of case 7 in various types of QFPs having various internal structures including the heat-spreader type QFP.

$$Rjc=L/(A\cdot\lambda_1)\times\beta(\lambda_2)^\alpha \quad (3)$$

$\lambda^1$ is the thermal conductivity of the material interposed between semiconductor chip 1 and the surface of case 7, L is the distance between the surfaces of the case and the semiconductor chip, A is the area of the semiconductor chip 1, and $\lambda_2$ is the thermal conductivity of the material interposed between semiconductor chip 1 and leadframe 2. In the case of a standard type (refer to FIG. 3A and FIG. 3B), thermal conductivities $\lambda_1$ and $\lambda_2$ are the thermal conductivity of resin 3. In the case of the enclosed heat-spreader type (refer to FIG. 3C), thermal conductivity $\lambda_1$ is the thermal conductivity of resin 3 and thermal conductivity $\lambda_2$ is the thermal conductivity of the copper plate making up heat spreader 10. In the case of the exposed heat-spreader type (refer to FIG. 3D), heat conductivities $\lambda_1$ and $\lambda_2$ are the heat conductivity of the copper plate making up heat spreader 10. The values $\beta$ (a constant) and $\alpha$ (a multiplier) are correction values for increasing accuracy.

Thermal resistance Rja can be accurately determined for both the standard type QFP and heat-spreader type QFP by inserting thermal resistance Rjc found by this equation (3) into the above-described equation (1).

By this thermal resistance calculating method, it is possible to determine the thermal resistance of a semiconductor package having a heat spreader more accurately than the prior art.

In addition, constant $\beta$ and multiplier $\alpha$ are set within the ranges $0.5<\beta<1.4$ and $-0.45<\alpha<0.2$, and preferably within the ranges $0.5<\beta<1.4$ and $-0.25<\alpha<0.03$. This constant $\beta$ and multiplier $\alpha$ are results obtained by trial and error in experimentation whereby the value of thermal resistance Rja, which is the final calculation, has an error of 20% or less under usual conditions. Multiplier $\alpha$ preferably decreases to the degree that constant $\beta$ increases, and the optimum range of multiplier $\alpha$ corresponding to constant $\beta$ is as follows.

| Constant $\beta$ | Multiplier $\alpha$ |
|---|---|
| 0.5 | −0.25 to 0.20 |
| 0.6 | −0.25 to 0.18 |
| 0.7 | −0.30 to 0.13 |
| 0.8 | −0.32 to 0.10 |
| 0.9 | −0.35 to 0.08 |
| 1.0 | −0.38 to 0.07 |
| 1.2 | −0.40 to 0.04 |
| 1.4 | −0.45 to 0.03 |

The calculation method is next described for a case in which the QFP and semiconductor chip are rectangular.

In the foregoing explanation, the package shape was assumed to be square, but rectangular QFP and semiconductor chips 1 are currently in wide use. So, as for a rectangular QFP, actual measurements were taken of each portion for this rectangular QFP and thermal resistance Rja is found by modeling based on these actual measurements, as in the example of the prior art (refer to FIG. 1). This rectangular QFP and semiconductor chip 1 were converted to a square having the same volume and modeled, and thermal resistance Rja was then calculated by using the above-described equation (1) and equation (3). Thermal resistance Rja was also found for this rectangular QFP by carrying out a three-dimensional heat-fluid simulation. The thermal resistance Rja found by these three methods were compared and found to be nearly the same in each case.

From these results, it can be seen that thermal resistance Rja is substantially equal for semiconductor packages have identical internal structure and volume. In other words, thermal resistance can be easily and accurately found for semiconductor chips or QFP of shapes other than squares such as rectangles through conversion to a square having the same volume and calculating thermal resistance Rja by using the above-described equations (1) and (3).

Figure 9:
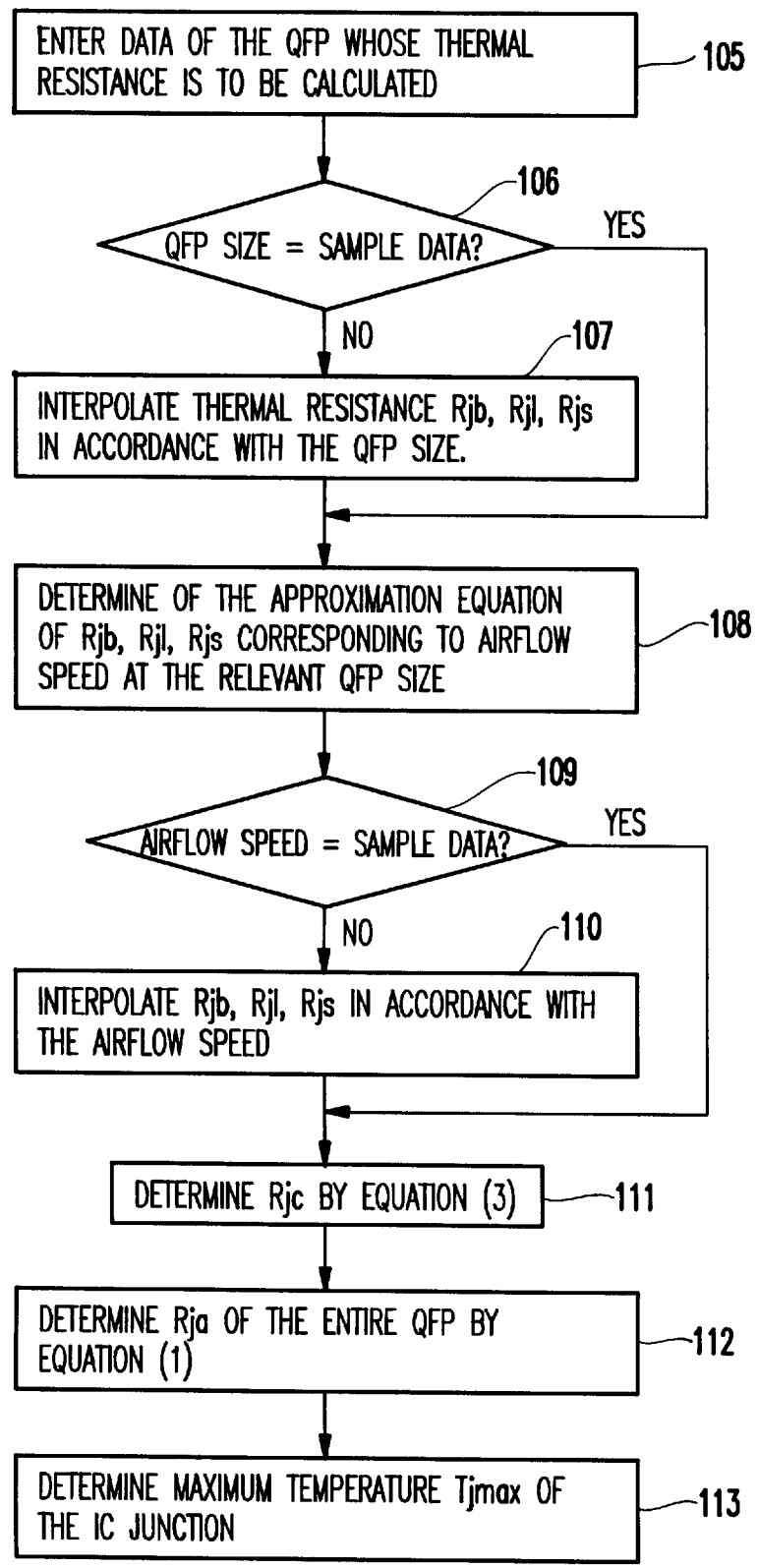
FIG. 9 is a flow chart showing the thermal resistance calculation steps of the thermal resistance calculating device of the present invention.

Explanation is next presented regarding a thermal resistance calculating device for actually carrying out the thermal resistance calculation described above. FIG. 7 is a block diagram showing the outline of this thermal resistance calculating device, FIG. 8 is a flow chart illustrating the preparatory steps for initialization of this thermal resistance calculating device, and FIG. 9 is a flow chart showing the actual thermal resistance calculation steps for finding thermal resistance Rja of various types of QFP which are carried out after completing the preparatory steps.

This thermal resistance calculating device is for obtaining thermal resistance Rja of various type QFPs with radiation fins and properties which is used under various conditions. This thermal resistance calculating device includes keyboard 21, CPU 22 for finding thermal resistance, display 23 for displaying results of calculations, and memory unit 24 for storing equations and data for carrying out processing. Detailed explanation is next presented regarding the steps for finding thermal resistance of QFP by using this thermal resistance calculating device.

As described hereinabove, thermal resistance Rja of various QFP can be accurately found by using equation (1) and equation (3). However, if actual measurements of temperatures and thermal analyses are rendered for each cases in order to determine each of the thermal resistance Rjb, Rjl, and Rjs of the three heat radiation paths (BOTTOM, LEAD, and SIDE paths) that are to be inserted in equation (1), it is impossible to solve the problems of the prior art, namely the process is troublesome, time-consuming, and unsuitable for wide use, and unsuitable to adapt to the products whose life cycle is shortened. The thermal resistance calculating device of the present invention, however, enables a simpler calculation because it does not necessitate actual temperature measurements for each of thermal resistance Rjb, Rjl, and Rjs of the three heat radiation paths for each individual case. This thermal resistance calculating device finds the thermal resistance Rjb, Rjl, and Rjs for each of a number of QFPs taken as samples in advance, stores the data of the samples, and calculating thermal resistance can be rendered by interpolating based on the data of the samples without such steps as actual temperature measurement.

The data of the samples is first found in the preparatory steps shown in FIG. 8. For example, thermal resistance Rjb, Rjl, and Rjs are found for each condition while varying conditions including the type of packages such as the standard-type and heat-spreader type, the size of the QFP, the airflow speed of cooling air from a separately installed cooling fan, and the presence or absence of radiation fins 11. In Step 101, the heat quantity ratios of the three heat radiation paths (BOTTOM, LEAD, and SIDE paths) are found through actual temperature measurements and thermal analyses under the 96 sets of conditions resulting from combination of the four previously described package types (refer to FIGS. 3A–3D); the four QFP sizes which are squares with each side of 10 (mm), 20 (mm), 30 (mm), and 40 (mm) respectively; the three airflow speeds of 1 (m/sec), 2 (m/sec), and 3 (m/sec); and the two options of the presence or absence of the radiation fins. In addition, thermal resistance Rja of the entire QFP is found through three-dimensional heat-fluid simulations under these 96 sets of conditions. Of these, the results relating to the condition of a 1 (m/sec) airflow speed for a standard-type QFP having copper alloy leadframe 2a is shown below.

Heat Quantity Ratios

| QFP without radiation fins | | | | |
|---|---|---|---|---|
| size (mm) | 10 | 20 | 30 | 40 |
| Rja (C/W) | 60 | 50 | 40 | 30 |
| Rjb (C/W) | 0.4 | 0.4 | 0.4 | 0.4 |
| Rjl (C/W) | 0.2 | 0.2 | 0.2 | 0.2 |
| Rjs (C/W) | 0.1 | 0.1 | 0.1 | 0.1 |

| QFP with radiation fins | | | | |
|---|---|---|---|---|
| size (mm) | 10 | 20 | 30 | 40 |
| Rja (C/W) | 40 | 30 | 20 | 10 |
| Rjb (C/W) | 0.2 | 0.2 | 0.2 | 0.2 |
| Rjl (C/W) | 0.1 | 0.1 | 0.1 | 0.1 |
| Rjs (C/W) | 0.1 | 0.1 | 0.1 | 0.1 |

In Step 102, thermal resistances Rjb, Rjl, and Rjs are next found under each of the conditions. These can each be found by dividing the thermal resistance Rja of the entire QFP by each heat quantity ratio. The results are as shown below.

Thermal Resistance

| QFP without radiation fins | | | | |
|---|---|---|---|---|
| size (mm) | 10 | 20 | 30 | 40 |
| Rjb (C/W) | 150 | 125 | 100 | 75 |
| Rjl (C/W) | 300 | 250 | 200 | 150 |
| Rjs (C/W) | 600 | 500 | 400 | 300 |

| QFP with radiation fins | | | | |
|---|---|---|---|---|
| size (mm) | 10 | 20 | 30 | 40 |
| Rjb (C/W) | 200 | 150 | 100 | 50 |
| Rjl (C/W) | 400 | 300 | 200 | 100 |
| Rjs (C/W) | 400 | 300 | 200 | 100 |

In this embodiment, the average value is found between the thermal resistance for a case in which radiation fins 11 are attached and the thermal resistance for a case in which radiation fins are not attached in Step 103. The results are as follows.

| size (mm) | 10 | 20 | 30 | 40 |
|---|---|---|---|---|
| Rjb (C/W) | 175 | 138 | 100 | 63 |
| Rjl (C/W) | 350 | 275 | 200 | 125 |
| Rjs (C/W) | 500 | 400 | 300 | 200 |

Figure 10C:
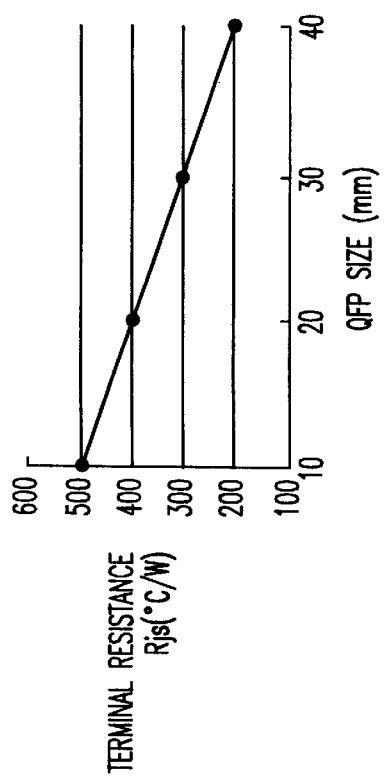
FIGS. 10A–10C are graphs showing the relation between QFP size and thermal resistance.
Figure 10A:
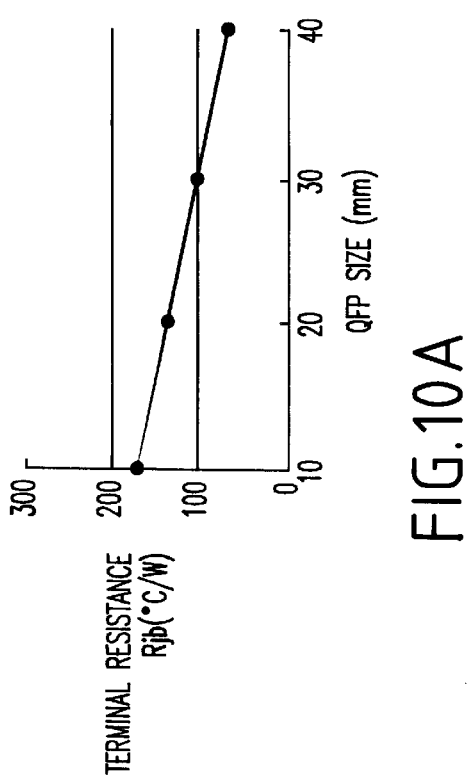
Figure 10B:
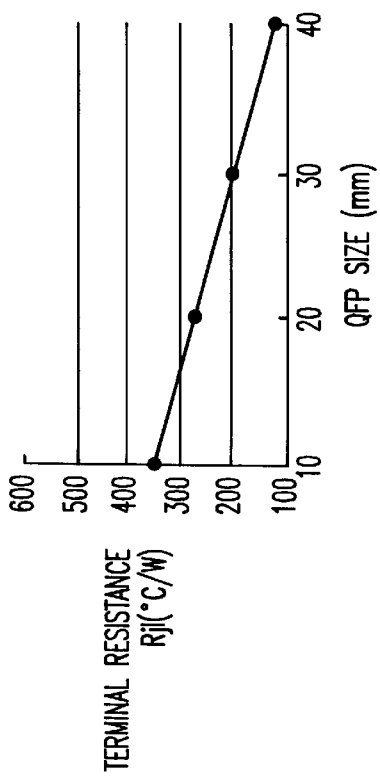

The relation is then found between the four QFP sizes and each of thermal resistance Rjb, Rjl, Rjs, (shown by the graphs in FIGS. 10A–10C), and in Step 104 an approximation equation is determined for finding the thermal resistance of sizes differing from those of the samples by interpolation. If the QFP size (the length of one side of a square) is y (mm).

$Rjb(y) = -3.75y + 212.5$ $Rjl(y) = -7.5y + 425$ $Rjs(y) = -10y + 600$

This approximation equation is stored in memory unit 24. The same process is carried out for the other package types.

The preparatory steps end with the completion of the initialization of the thermal resistance calculating device as described above, and the thermal resistance calculating device is completed at this time.

Explanation is next presented regarding the thermal resistance calculation steps (refer to FIG. 9) for finding thermal resistance Rja of a QFP that is the actual object of thermal resistance calculation by using the thermal resistance calculating device that has been completed through the preparatory steps (refer to FIG. 8).

Data are first entered by way of keyboard 21 in Step 105. In this embodiment, the following data are entered: the ambient temperature in which the QFP that is the object of thermal resistance calculation is used, the power consumption of the QFP, the airflow speed of cooling air, the thermal resistance Rca of the attached radiation fin unit, the QFP size (the length of one side when converted to a square having the same volume), and the size of semiconductor chip 1. The thermal conductivity of resin 3 that fills the inside of case 7 and, in a case in which heat spreader 10 is used, the thermal conductivity of heat spreader 10 are also entered as necessary. These conductivity need not be entered if they are same as thermal conductivity that are already stored, and they are entered only if they differ from stored thermal conductivity or if thermal conductivity are not stored at all. In this particular case, the QFP size is 35 (mm), the airflow speed is 1.5 (m/sec), the thermal conductivity of resin 3 inside case 7 is 0.6 (W/mk), and the thermal conductivity of heat spreader 10 is 395 (W/mk).

If the QFP size of the entered data is not same as the sample data (10 mm, 20 mm, 30 mm, or 40 mm) in Step 106, each of thermal resistance Rjb (y), Rjl (y), and Rjs (y) are found in Step 107 by interpolating using the approximation equation found and stored in memory unit 24 in Step 104. For example, the QFP size is 35 mm.

$Rjb(y) = -3.75 \times 35 + 212.5 = 81.25$ (° C./W)

$Rjl(y) = -7.5 \times 35 + 425 = 162.5$ (° C./W)

$Rjs(y) = -10 \times 35 + 600 = 250$ (° C./W)

These calculations are for a case in which the airflow speed is 1 (m/sec), so interpolation is necessary for cases in which the airflow speed is also different. Although not shown in the figures, data are taken for the airflow speeds 1 (m/sec), 2 (m/sec), and 3 (m/sec) with respect to the four QFP sizes 10 (mm), 20 (mm), 30 (mm), and 40 (mm) in Steps 101–103 of the preparatory steps. Analogizing from these data, thermal resistances Rjb, Rjl, and Rjs at airflow speeds of 1 (m/sec), 2 (m/sec), and 3 (m/sec) and with this QFP size (35 mm) can be derived as follows.

| 35 mm Copper Alloy QFP | | | |
|---|---|---|---|
| airflow speed | 1.0 m/sec | 2.0 m/sec | 3.0 m/sec |
| Rjb (C/W) | 81.25 | 80.25 | 79.25 |
| Rjl (C/W) | 162.5 | 161.5 | 160.5 |
| Rjs (C/W) | 250 | 240 | 230 |

The approximation equation for thermal resistances Rjb, Rjl, and Rjs corresponding to airflow speed x is found from this table in Step 108, as shown below.

$$Rjb = 1 \cdot 10^{-13} \cdot x^2 - x + 82.25$$

$$Rjl = 2 \cdot 10^{-13} \cdot x^2 - x + 163.5$$

$$Rjs = -10x + 260$$

Then, in cases in which the airflow speed is not same as the sample data (1 m/sec, 2 m/sec, 3 m/sec) in Step 109, thermal resistance Rjb, Rjl and Rjs are found in Step 110 by interpolation by using the approximation equation found in Step 107. Results of interpolation for a case in which the airflow speed is 1.5 (m/sec) are as follows.

$$Rjb = 1 \cdot 10^{-13} \cdot (1.5)^2 - 1.5 + 82.25 = 80.75$$

$$Rjl = 2 \cdot 10^{-13} \cdot (1.5)^2 - 1.5 + 163.5 = 162$$

$$Rjs = -10 \cdot 1.5 + 260 = 245$$

The thermal resistance Rjb, Rjl, and Rjs of the three heat radiation paths (BOTTOM, LEAD, and SIDE paths) can thus be found.

In cases in which the QFP size is same as sample data (10 mm, 20 mm, 30 mm, 40 mm) in Step 106, data stored in memory unit 24 can be used as is and Step 107 need not be carried out. Similarly, in cases in which the airflow speed is same as sample data (1 m/sec, 2 m/sec, 3 m/sec) in Step 109, the data stored in memory unit 24 can be used as is and Step 110 need not be carried out.

In Step 111, thermal resistance Rjc is found by CPU 22 by using equation (3) stored in the memory unit 24. In this case, β is set to 1.0 and α is set to −0.09. These values α and β have been set in advance within the ranges 0.5<β<1.4 and −0.45<α<0.2. It is also clear from the semiconductor chip size entered in Step 105 that the distance L between the top surface of semiconductor chip 1 and the surface of case 7 is 0.001 (m), and semiconductor chip area A is 0.0001 (m²). Accordingly, thermal resistance Rjc is as follows.

$$Rjc = L/(A \cdot \lambda_1) \times 1.0 \times 0.6^{-0.09}$$

$$= 0.001/(0.0001 \times 0.6) \times 1.0 \times 0.6^{-0.09}$$

$$= 17.4 \ (° \ C./W)$$

In Step 112, thermal resistance Rja of the entire QFP is found by CPU 22 by means of equation (1) stored in the memory unit. As described hereinabove, thermal resistance Rca of the radiation fins 11 unit (Rca=13.7) is entered in Step 105, thermal resistance Rjb, Rjl, Rjs (Rjb=80.75, Rjl=162, and Rjs=245) are calculated in Step 110, and thermal resistance Rjc between the top surface of semiconductor chip 1 and the surface of case 7 (Rjc=17.4) is calculated in Step 111. Accordingly, 1/Rja is as follows.

$$1/Rja = 1/(17.4 + 13.7) + 1/80.75 + 1/162 + 1/245$$

$$Rja = 18.25$$

This completes the determination of thermal resistance Rja of a QFP with radiation fins 11 mounted.

The above-described example relates to a standard type QFP having copper alloy leadframe 2b (refer to FIG. 3B), but thermal resistance Rja is found in the same way for a standard type QFP having 42-alloy leadframe 2a (refer to FIG. 3A), an enclosed heat-spreader type QFP (refer to FIG. 3C), or an exposed heat-spreader type QFP (refer to FIG. 3D). Four thermal resistance Rja are displayed on display 23 for a QFP size of 35 mm and an airflow speed of 1.5 m/sec as for these four types of QFP.

If actual measurements and thermal analyses are carried out for a number of representative samples in this way, thermal resistance can be found by an extremely simple calculation for various types of semiconductor packages and under various experimental conditions.

In this embodiment, moreover, maximum temperature Tjmax of an IC junction (the heat generating portion of a semiconductor chip) is found in Step 113. Although not described here in detail, maximum temperature Tjmax is found by a equation of first or higher degree concerning airflow speed, and is determined according to the ambient temperature and power consumption entered in Step 105 and thermal resistance Rja found in Step 112. This maximum temperature Tjmax is displayed on display 23 for the four types of QFP in the same way as thermal resistance Rja.

In the preparatory steps of this embodiment, the heat quantity ratios of each of the heat radiation paths are divided by the thermal resistance of the entire QFP to find the thermal resistance of the three heat radiation paths (BOTTOM, LEAD, and SIDE paths) which are the sample data. If the thermal resistance of the three heat radiation paths (BOTTOM, LEAD, and SIDE paths) which are the sample data can be found directly, however, there is no need to find the heat quantity ratios and thermal resistance of the entire QFP by means of three-dimensional heat-fluid simulation, and Steps 101–103 can be simplified. Although the average value of thermal resistance for a case in which radiation fins are present and a case in which there are no radiation fins is taken as sample data in this embodiment, just one thermal resistance for either a case in which radiation fins are present or a case in which there are no radiation fins can be set as the sample data and thermal resistance for the other case need not be found, in which case, the data to be obtained is reduced by half and the process is simplified.

Figure 11:
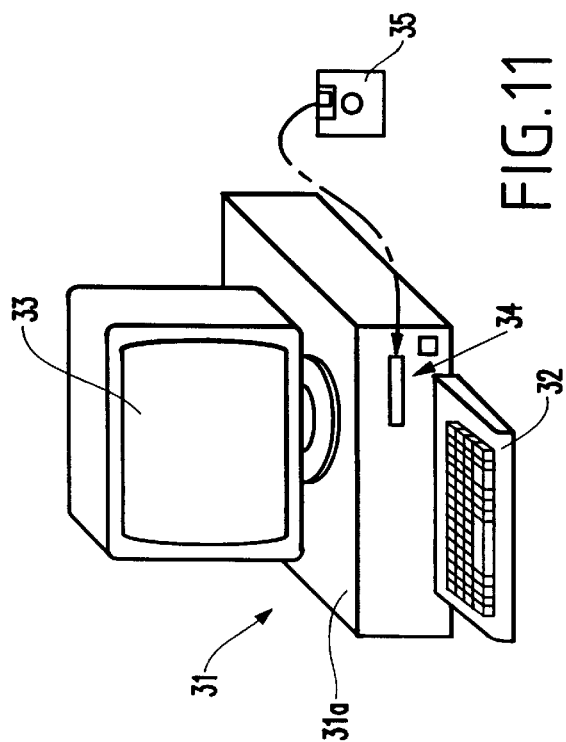
FIG. 11 is a reduced perspective view of a recording medium of the present invention and a personal computer using the recording medium.

Explanation is next presented with reference to FIG. 11 regarding execution of the above-described thermal resistance calculation by a personal computer.

This personal computer 31 is provided with keyboard 32, CPU 31a that can carry out general calculations, display 33, and disk drive 34. Sample data, which are the results of the preparatory steps (refer to FIG. 8) carried out in advance, equations (1) and (3), an approximation equation for interpolation, and a program for executing these calculations by a CPU 31a based on these equations are stored on a recording medium (such as a floppy disk, CD-ROM, MO, etc.) 35 that can be inserted an read in disk drive 34. Accordingly, when the user first enters such conditions as QFP size, airflow speed, power consumption, and ambient temperature from keyboard 32 as in Step 101, CPU 31a of personal computer 31, which is controlled by the program, calculates thermal resistance Rja and maximum temperature Tjmax of IC junction based on each equation and sample data stored on recording medium 35 as in Steps 112 and 113, and displays the results on display 33. The use of this recording medium 35 allows the thermal resistance calculation to be readily executed by using any generally available personal computer 31 without requiring the use of a dedicated thermal resistance calculating device. Moreover, a relatively small amount of data is recorded on recording medium 35, and a typical floppy disk in general use can therefore be employed.

The present invention thus allows determination of the thermal resistance of a QFP made as a unit with radiation fins, thus enabling appropriate design of an electrical component or cooling device.

In addition, if sample data are found in advance by carrying out actual measurements and thermal analyses for a number of samples, the thermal resistance of a QFP with radiation fins can be quickly and easily calculated by merely entering a limited small number of conditions such as QFP size and the airflow speed of cooling air for QFP of various structures. A person lacking specialized expertise can therefore readily calculate the thermal resistance of a QFP equipped with radiation fins without actually fabricating the product and without carrying out a complex analysis such as three-dimensional heat-fluid simulation. The present invention therefore enables analysis of the dependency of the thermal resistance upon parameters such as the size or material of the QFP and the airflow speed of cooling air as well as the proper selection of radiation fins, even in the absence of an actual QFP, whereby appropriate design of cooling devices can be achieved.

In addition, the data and program necessary for this thermal resistance calculation have a relatively small volume and can be stored on an ordinary recording medium, and when this recording medium is used, the thermal resistance calculation can be easily executed on a widely available personal computer.

While a preferred embodiment of the present invention has been described using specific terms, such description is for illustrative purposes only, and it is to be understood that changes and variations may be made without departing from the spirit or scope of the following claims.

What is claimed is:

1. A method of calculating thermal resistance of a semiconductor package accommodating a semiconductor chip within a case, said method comprising a step of finding thermal resistance of said semiconductor package in which radiation fins are mounted on the surface of said case, based on the thermal resistance of a heat radiation path passing through the bottom surface of said case, thermal resistance of a heat radiation path passing through a leadframe, thermal resistance of a heat radiation path passing through sides of said case other than said leadframe, thermal resistance between said semiconductor chip and the surface of said case, and thermal resistance of said radiation fins.

2. A method of calculating thermal resistance according to claim 1 wherein thermal resistance of said semiconductor package is found by the following equation:

$$1/Rja = [1/(Rjc+Rca)] + 1/Rjb + 1/Rjl + 1/Rjs$$

where $Rja$ is the thermal resistance of said semiconductor package in which said radiation fins are mounted on the surface of said case, $Rjb$ is the thermal resistance of the heat radiation path passing through the bottom surface of said case, $Rjl$ is the thermal resistance of the heat radiation path passing through said leadframe, $Rjs$ is the thermal resistance of the heat radiation path passing through the sides of said case other than said leadframe, $Rjc$ is the thermal resistance between said semiconductor chip and the surface of said case, and $Rca$ is the thermal resistance of said radiation fins.

3. A method of calculating thermal resistance according to claim 1 further comprising the step of finding the thermal resistance between said semiconductor chip and the surface of said case based on the thermal conductivity of material interposed between said semiconductor chip and the surface of said case and the thermal conductivity of material interposed between said semiconductor chip and said leadframe.

4. A method of calculating thermal resistance according to claim 3 wherein the thermal resistance between said semiconductor chip and the surface of said case is found by the following equation:

$$Rjc = L/(A \cdot \lambda_1) \times \beta \cdot \lambda_2^\alpha$$

where $Rjc$ is the thermal resistance between said semiconductor chip and the surface of said case, $\lambda_1$ is the thermal conductivity of the material interposed between said semiconductor chip and the surface of said case, $\lambda_2$ is the thermal conductivity of the material interposed between said semiconductor chip and said leadframe, $A$ is area of said semiconductor chip, $L$ is distance between said semiconductor and the surface of said case, $\alpha$ is a multiplier within the range $-0.45 < \alpha < 0.2$, and $\beta$ is a constant within the range $0.5 < \beta < 1.4$.

5. A method of calculating thermal resistance according to claim 4 wherein $\alpha$ is within the range $-0.25 < \alpha < 0.03$.

6. A method of calculating thermal resistance according to claim 4 wherein the value of $\alpha$ decreases as the value of $\beta$ increases.

7. A method of calculating thermal resistance according to claim 1 further comprising steps of:

taking a plurality of said semiconductor packages of different sizes as samples and predetermining by actual measurements and thermal analyses each of the thermal resistance of the heat radiation path passing through the bottom surface of said case, the heat radiation path passing through said leadframe, and the heat radiation path passing through sides of said case other than said leadframe; and interpolating based on said predetermined thermal resistances of said samples for the thermal resistances of said three heat radiation paths of said semiconductor package having a size different from the sizes of said samples.

8. A method of calculating thermal resistance according to claim 1 further comprising the steps of:

finding in advance by actual measurements and thermal analyses thermal resistance of the heat radiation path passing through the bottom surface of said case, the heat radiation path passing through said leadframe, and the heat radiation path passing through sides of said case other than said leadframe of said semiconductor package under a plurality of conditions having differing cooling airflow speeds as sample data; and interpolating based on said sample data for thermal resistances of said three heat radiation paths of said semiconductor package under conditions in which airflow speed differs from that of any of said sample data.

9. A method of calculating thermal resistance according to claim 1 wherein, for said semiconductor package having a shape other than a square, thermal resistance of said semiconductor package is found by converting to a square of the same volume.

10. A method of calculating thermal resistance according to claim 1 wherein thermal resistance $Rja$ of said semiconductor package with said radiation fins mounted is found for each of a case in which said semiconductor package does not include a heat spreader, a case in which said semiconductor package includes an enclosed heat spreader, and a case in which said semiconductor package includes an exposed heat spreader.

11. A method of calculating thermal resistance according to claim 10 wherein thermal resistance of said semiconductor package with said radiation fins mounted is further found for each of a case in which said semiconductor package lacks a heat spreader and said leadframe is made of 42-iron nickel alloy, and a case in which said semiconductor package lacks a heat spreader and said leadframe is made of a copper alloy.

12. A method of calculating thermal resistance of a semiconductor package that accommodates a semiconductor chip within a case, comprising a step of finding thermal resistance between said semiconductor chip and the surface of said case based on thermal conductivity of a material interposed between said semiconductor chip and the surface of said case and thermal conductivity of a material interposed between said semiconductor chip and a leadframe.

13. A method of calculating thermal resistance according to claim 12 wherein thermal resistance between said semiconductor chip and the surface of said case is found by the following equation:

$$Rjc = L/(A \cdot \lambda_1) \times \beta \cdot \lambda_2^{\alpha}$$

where Rjc is thermal resistance between said semiconductor chip and the surface of said case, $\lambda_1$ is the thermal conductivity of the material interposed between said semiconductor chip and the surface of said case, $\lambda_2$ is the thermal conductivity of the material interposed between said semiconductor chip and said leadframe, A is area of said semiconductor chip, L is distance between said semiconductor and said surface of said case, $\alpha$ is a multiplier within the range $-0.45 < \alpha < 0.2$, and $\beta$ is a constant within the range $0.5 < \beta < 1.4$.

14. A method of calculating thermal resistance according to claim 13 wherein $\alpha$ is within the range $-0.25 < \alpha < 0.03$ and $\beta$ is within the range $0.5 < \beta < 1.4$.

15. A method of calculating thermal resistance according to claim 14 wherein the value of $\alpha$ decreases as the value of $\beta$ increases.

16. A thermal resistance calculating device comprising:

input means for entering at least a size of a semiconductor package, a size of a semiconductor chip, and a thermal resistance of radiation fins;

processing means for finding thermal resistance of said semiconductor package with said radiation fins mounted based on a method of calculating thermal resistance of a semiconductor package that accommodates a semiconductor chip within a case that includes a step of finding thermal resistance of said semiconductor package in which radiation fins are mounted on the surface of said case from thermal resistance of a heat radiation path passing through the bottom surface of said case, thermal resistance of a heat radiation path passing through a leadframe, thermal resistance of a heat radiation path passing through side portions other than said leadframe, thermal resistance between said semiconductor chip and the surface of said case, and thermal resistance of said radiation fins; and display means for displaying thermal resistance of said semiconductor package found by said processing means.

17. A thermal resistance calculating device comprising:

input means for entering at least a size of a semiconductor chip; and processing means for finding thermal resistance between said semiconductor chip and the surface of a case based on a method of calculating thermal resistance of a semiconductor package accommodating a semiconductor chip within said case that comprises steps of finding thermal resistance between said semiconductor chip and the surface of said case from thermal conductivity of a material interposed between said semiconductor chip and the surface of said case and thermal conductivity of a material interposed between said semiconductor chip and a leadframe.

* * * * *